US006623695B2

(12) United States Patent
Malchesky et al.

(10) Patent No.: US 6,623,695 B2
(45) Date of Patent: *Sep. 23, 2003

(54) CHEMICAL MODIFICATION OF ELECTROCHEMICALLY ACTIVATED SOLUTIONS FOR IMPROVED PERFORMANCE

(75) Inventors: Paul S. Malchesky, Painesville Twp., OH (US); Christopher M. Fricker, Concord, OH (US)

(73) Assignee: Steris Corporation, Mentor, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/428,207

(22) Filed: Oct. 27, 1999

(65) Prior Publication Data

US 2003/0049163 A1 Mar. 13, 2003

Related U.S. Application Data

(63) Continuation-in-part of application No. 08/984,752, filed on Dec. 4, 1997, now abandoned.

(51) Int. Cl.[7] .................... C23F 11/00; B01J 19/08; C11D 17/00; B01D 17/06; B08B 9/00
(52) U.S. Cl. ..................... 422/12; 422/7; 422/32; 422/34; 422/186; 422/292; 510/161; 510/401; 510/421; 510/426; 510/480; 510/512; 210/243; 210/748; 134/22.1; 134/22.16; 134/26; 134/28; 134/36; 134/41
(58) Field of Search ................ 510/161, 401, 510/405, 480, 512, 421, 426; 422/6, 7, 12, 19, 28, 31–32, 34, 36, 40, 292, 186; 139/22.1, 22.11, 22.13, 22.14, 22.16, 22.17, 22.19, 26, 28, 36, 41, 42; 210/748, 243

(56) References Cited

U.S. PATENT DOCUMENTS

| | | | |
|---|---|---|---|
| 3,766,037 A | * 10/1973 | Lee | 204/152 |
| 3,895,910 A | 7/1975 | Juchniewicz | 21/27 R |
| 3,975,246 A | 8/1976 | Eibl et al. | 204/151 |
| 4,470,890 A | 9/1984 | Bommaraju et al. | 204/98 |
| 4,710,233 A | 12/1987 | Hohmann et al. | 134/1 |
| 5,037,623 A | 8/1991 | Schneider et al. | 422/292 |
| 5,077,008 A | 12/1991 | Kralovic et al. | 422/37 |
| 5,091,343 A | 2/1992 | Schneider et al. | 422/297 |
| 5,116,575 A | 5/1992 | Badertscher et al. | 422/28 |
| 5,334,383 A | 8/1994 | Morrow | 424/94.4 |
| 5,350,563 A | 9/1994 | Kralovic et al. | 422/28 |
| 5,427,667 A | 6/1995 | Bakhir et al. | 204/260 |
| 5,487,788 A | 1/1996 | Kamiya et al. | 134/1 |
| 5,507,932 A | 4/1996 | Robinson | 204/228 |
| 5,560,816 A | 10/1996 | Robinson | 205/687 |
| 5,622,848 A | 4/1997 | Morrow | 435/173.1 |
| 5,624,636 A | 4/1997 | Schwartz | 422/37 |
| 5,628,888 A | 5/1997 | Bakhir et al. | 204/260 |
| 5,635,040 A | 6/1997 | Bakhir et al. | 204/260 |
| 5,723,095 A | * 3/1998 | Fricker et al. | 422/292 |
| 5,759,489 A | * 6/1998 | Miura et al. | 422/28 |
| 5,932,171 A | * 8/1999 | Malchesky | |
| 5,938,915 A | * 8/1999 | Morisawa | 205/464 |
| 6,022,512 A | * 2/2000 | Tanaka et al. | 422/292 |
| 6,143,443 A | * 11/2000 | Kazacos et al. | 429/204 |

FOREIGN PATENT DOCUMENTS

| | | |
|---|---|---|
| DE | 4418812 | 12/1995 |
| DE | 19534925 | 3/1997 |
| EP | 706801 | 4/1996 |
| EP | 722740 | 7/1996 |
| ES | 2092956 | 12/1996 |
| GB | 2294473 | 5/1996 |
| JP | 7327674 | 12/1995 |
| JP | 7328100 | 12/1995 |
| JP | 7328638 | 12/1995 |
| JP | 8038582 | 2/1996 |
| JP | 8052475 | 2/1996 |
| JP | 8082776 | 3/1996 |
| JP | 8085891 | 4/1996 |
| JP | 8089968 | 4/1996 |

(List continued on next page.)

OTHER PUBLICATIONS

Pembrook, L., "Novel Method for Disinfection of Endoscopes in Japan Utilizes Acidic Electrolytic Water," Gastroenterology and Endoscopy News, Aug. 1997, p. 8.

Shimizu, Yoshinobu, Sugawara, Hiroko, "Virucidal and Bactericidal Effects of Electrolyzed Oxidizing Water: Comparison of Disinfectant Effect with Electrolyzed Oxidizing Water and Hypochlorous Acid," Jpn. J. Oral Biol., 38, 1996, p. 564–571.

Pal'chitskij, A.M.; Malakhova, T.S., "Efficiency of Treatment and Disinfection of Sewage from Viruses," Elektrovyaz v 17 n 8 AugyDec 1996, p. 656–661 (*English Abstract*).

Sterox brochure.

"Who Says Electricity and Water Don't Mix", Enviro–Chem Systems, Monsanto.

Primary Examiner—Robert J. Warden, Sr.
Assistant Examiner—Monzer R. Chorbaji
(74) Attorney, Agent, or Firm—Fay, Sharpe, Fagan, Minnich & McKee, LLP

(57) ABSTRACT

An anticorrosive, penetration enhancing composition for cleaning decontaminating and rinsing includes electrochemically activated (ECA) water as the decontamination agent. The anticorrosive decontamination composition has, as the anticorrosive agent, a compound or mixture of compounds capable of inhibiting corrosion of various metals used in sterilization decontamination and rinsing systems and objects such as medical instruments. Preferred anticorrosive compounds include phosphates, azoles, and sulfates. Other additives, including wetting agents, are added to reduce the surface energy of the ECA water. This reduced surface energy permits the ECA water to penetrate into objects of complex design thus permitting complete decontamination of the treated object.

28 Claims, No Drawings

| | FOREIGN PATENT DOCUMENTS | | |
|---|---|---|---|
| JP | 8119605 | 5/1996 |
| JP | 8126886 | 5/1996 |
| JP | 8126889 | 5/1996 |
| JP | 8127886 | 5/1996 |
| JP | 8150392 | 5/1996 |
| JP | 8150325 | 6/1996 |
| JP | 8155459 | 6/1996 |
| JP | 8283714 | 10/1996 |
| JP | 8290159 | 11/1996 |
| JP | 8294689 | 11/1996 |
| JP | 8296076 | 11/1996 |
| JP | 8299961 | 11/1996 |
| JP | 8302792 | 11/1996 |
| JP | 8308909 | 11/1996 |
| JP | 8308910 | 11/1996 |
| JP | 8309359 | 11/1996 |
| JP | 8318278 | 12/1996 |
| JP | 8318279 | 12/1996 |
| JP | 8323364 | 12/1996 |
| JP | 8323366 | 12/1996 |
| JP | 8327955 | 12/1996 |
| JP | 9047763 | 2/1997 |
| JP | 9056614 | 3/1997 |
| JP | 9058747 | 3/1997 |
| JP | 9066064 | 3/1997 |
| JP | 9066100 | 3/1997 |
| JP | 9067261 | 3/1997 |
| RU | 2045480 | 10/1995 |
| RU | 2045962 | 10/1995 |
| RU | 2045963 | 10/1995 |
| RU | 2047569 | 11/1995 |
| RU | 2057546 | 4/1996 |
| RU | 2057821 | 4/1996 |
| WO | WO 9711908 | 4/1997 |

\* cited by examiner

CHEMICAL MODIFICATION OF ELECTROCHEMICALLY ACTIVATED SOLUTIONS FOR IMPROVED PERFORMANCE

This application is a continuation-in-part of U.S. application Ser. No. 08/984,752, filed Dec. 4, 1997 now abandoned.

BACKGROUND OF THE INVENTION

The present invention relates to the decontamination and cleaning arts. It finds particular application in conjunction with the decontamination of medical instruments and equipment. It will be appreciated, however, that the invention is also applicable to the microbial decontamination, including disinfection or sterilization, of other articles such as food processing equipment, pharmaceutical processing equipment, animal cages, and other equipment.

Various methods and apparatus are known for decontaminating and/or sterilizing medical instruments and devices. For example, medical instruments and other devices are commonly sterilized in a steam autoclave. Autoclaves kill life forms with a combination of high temperature and high pressure. However, steam autoclaves have several drawbacks. The pressure vessels are bulky and heavy. Also, the high temperature and pressure tend to reduce the useful life of medical devices having rubber and plastic components. The medical devices must be precleaned before being placed in the autoclave to remove bodily tissues and fluids. Moreover, the autoclave sterilization and cool-down cycles take an excessive amount of time, especially in light of the need to minimize the "down time" of expensive, reusable medical devices.

Another known sterilization method utilizes ethylene oxide gas. Ethylene oxide gas sterilization and aeration cycles are even longer than steam autoclave sterilization and cool-down cycles. Ethylene oxide is also hazardous to humans and, therefore, environmental concerns are associated with its use.

Low temperature liquid disinfection and sterilization devices are also known. These devices typically utilize one of several known liquid anti-microbial solutions such as peracetic acid, glutaraldehyde, alcohol, aqueous hydrogen peroxide, and the like. In general, these low temperature liquid systems have been found to be effective. However, hospitals and other health care facilities continue to demand improved sterilization effectiveness and efficiency to reduce the risk of infection and to reduce the percentage of time that expensive medical devices are out of use for sterilization procedures. Also, certain low temperature liquid anti-microbial solutions have fallen out of favor. For example, the use of glutaraldehyde presents environmental concerns and also requires an excessively long cycle time to sterilize, rather than simply disinfect, medical devices. The environmentally harmful glutaraldehyde must be specially disposed of, increasing the cost of sterilization. Other agents, such as alcohols, have been found to be destructive to certain plastic components of medical instruments.

Recently, there has been an increased emphasis on the effective cleaning of post-operative debris from the medical instruments and devices. Most known sterilization equipment require that the contaminated medical devices be precleaned before the sterilization cycle. Others simply sterilize without regard to cleaning which results in a sterile device having sterile debris adhered thereto.

Certain sterilization devices rely upon the filtering of water with a 0.2 $\mu$m or smaller pore size microbe-removal filter media to provide a sterile rinse liquid. However, it would be desirable to provide an additional safeguard against the recontamination of medical devices with rinse liquid by ensuring a virus-free rinse solution. A virus-free rinse solution may not be assured with simple filtration of the rinse liquid. Therefore, there has been found a need to provide a sterilization apparatus that ensures a bacteria and virus free rinse liquid to prevent the accidental recontamination of the sterilized medical device during rinsing operations.

Most recently, the cleaning and decontamination properties of solutions formed via the electrolysis of water under special conditions have been explored. Electrolysis devices are known which receive a supply of water, such as tap water, commonly doped with a salt, and perform electrolysis on the water to produce (I) an anolyte produced at the anode of the electrolysis unit; and, (ii) and catholyte produced at the cathode of the electrolysis unit. The anolyte and catholyte may be used individually or as a combination. The anolyte has been found to have anti-microbial properties, including anti-viral properties. The catholyte has been found to have cleaning properties.

To create these anolyte and catholyte solutions, tap water, often with an added electrically conducting agent such as halogen salts including the salts sodium chloride and potassium chloride, is passed through an electrolysis unit or module which has at least one anode chamber and at least one cathode chamber which may be separated from each other by a membrane. An anode contacts the water flowing in the anode chamber, while the cathode contacts the water flowing in the cathode chamber. The anode and cathode are connected across a source of electrical potential to expose the water to an electrical field. The membrane may allow the transfer of electron carrying species between the anode and the cathode but limits fluid transfer between the anode and cathode chambers. The salt and minerals naturally present in and/or added to the tap water undergo oxidation in the anode chamber and reduction in the cathode chamber. The solution resulting at the anode (anolyte) and the solution resulting at the cathode (catholyte) remain separate or are recombined and can be used for a wide variety of different purposes.

However, electrochemically activated (ECA) water is not without shortcomings. ECA waters have high surface energies comparable to the incoming water. The high surface energies of ECA water have been found to cause lower penetration ability of the ECA water. In the medical instrument field, for example, high penetration ability is desired due to the complex nature of medical instruments. A sterilant must be able to penetrate even the smallest crevices in order to ensure the sterility of the instrument. The high surface energy of ECA water does not allow for penetration of the ECA water into creviced areas of medical instruments. Thus, complete kill may not be achieved.

Further problems have arisen on metal surfaces coming into contact with the ECA water, including the sterilization equipment and metal medical devices. The ECA water is corrosive to metal. Stainless steel, used to produce many medical devices, is particularly susceptible to corrosion by ECA water.

ECA water as a decontamination and cleaning agent can therefore produce some results which are problematic when decontaminating complex metal objects such as stainless steel medical equipment.

The present invention contemplates an improved ECA water solution. The improved ECA water solution has enhanced penetration ability and reduced corrosiveness compared to prior ECA water solutions.

SUMMARY OF THE INVENTION

In accordance with a first aspect of the present invention, an anticorrosive composition for cleaning and decontaminating is provided which comprises electrochemically activated (ECA) water as the decontamination agent. The anticorrosive decontamination composition has, as the anticorrosive agent, a compound or mixture of compounds capable of inhibiting corrosion of various metals used in sterilization systems and objects such as medical instruments.

In accordance with another aspect of the invention, other additives, including wetting agents, are added to reduce the surface energy of the ECA water. This reduced surface energy permits the ECA water to penetrate into complex objects thus permitting complete decontamination of the treated object.

A further aspect of the invention includes a method for decontamination of metal objects, including medical equipment, by using ECA water which contains anticorrosive agents. The ECA water may additionally contain wetting agents to enhance penetration of the ECA water into crevices of objects to be treated. This assures complete decontamination of the treated object.

One advantage of the present composition is that metal objects may be effectively decontaminated using ECA water with considerably reduced metal corrosion.

Another advantage of the present invention resides in its improved solution penetration into complex objects due to lower surface energy of the solution.

A further advantage relates to the use of the treated ECA water as a final rinse solution in a sterilization apparatus without corroding the sterilization apparatus or instruments being sterilized therein.

Still other advantages and benefits of the invention will become apparent to those skilled in the art upon a reading and understanding of the following detailed description of the preferred embodiments.

DETAILED DESCRIPTION OF THE PREFERRED EMBODIMENTS

Water to be used in a sterilization procedure is introduced into a suitable water electrolysis apparatus. Such an apparatus includes at least one electrolysis unit or module having an anode chamber and a cathode chamber and may be separated by a membrane. The membrane, if present, divides the water into two parts, a first part in the anode chamber and a second part in the cathode chamber. In flow through systems, incoming water is divided into two flows that are channeled to the anode and cathode chambers, respectively. Examples of such water electrolysis units are as described in U.S. Pat. Nos. 5,635,040; 5,628,888; 5,427,667; 5,334,383; 5,507,932; 5,560,816; and 5,622,848 whose disclosures are incorporated herein by reference. Any other suitable water electrolysis units may be used, including an electrolysis unit that utilizes a batch type electrochemical activation. The invention is not meant to be limited to any particular electrolysis apparatus.

The electrode chamber of an electrolysis unit includes an anode electrode and a cathode electrode that contacts the passing water. The membrane, if present, prevents the anolyte and catholyte from mixing. The membrane allows electron carrying species to transfer between the anode and cathode chambers. A source of electric potential is connected across the anode and the cathode to expose the water to an electric field that produces an oxidation reaction at the anode and a reduction reaction at the cathode. These reactions convert the water into an anolyte solution and a catholyte solution. If desired, first and second reservoirs or holding tanks may be provided in fluid communication with the outlets of the chambers in a system separating the anolyte and catholyte to hold the catholyte and anolyte solutions, respectively, as they are produced so that these solutions may be used subsequently for decontamination and/or cleaning, including disinfection, sterilization, and rinsing operations.

In a first embodiment, corrosion inhibiting and surface energy reducing additives are introduced into the water prior to or during electrolysis. The corrosion inhibitors and surface energy reducing additives which are added to the water prior to or during the electrolysis are those which are not decomposed upon passage through the electrolysis unit. Consequently, the additives, such as corrosion inhibitors, retain their anticorrosive activity upon circulation through the electrolysis unit. Further, the ECA water's decontamination properties are not compromised by the inclusion of the additives prior to or during electrochemical activation of the water.

In a second embodiment, the additives (corrosion inhibitors and/or surface energy reducing agents) are added after electrolysis. If added after electrolysis, the additives may be added to the catholyte or the anolyte. Other additives, including, but not limited to, detergents and pH buffers, may also be added to the catholyte and/or anolyte solution.

The corrosion inhibitory agents are selected in accordance with the nature of the materials in the items being cleaned and/or decontaminated with the electrochemically activated water. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

The copper and brass corrosion inhibitors include triazoles, azoles, benzoates, tolyltriazoles, dimercaptothiadiazoles, and other five-membered ring compounds. Preferably, the copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, the phosphates tend to cause calcium and magnesium salts present in hard water to precipitate and coat the instruments being decontaminated and/or cleaned and also leaves deposits on parts of the electrolysis system. A sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated.

However, to ensure universal applicability with any water that might be utilized, the presence of a sequestering agent is preferred. It is noted that the sequestering agent can be added to the water prior to, during or after electrochemical activation of the water without any negative impact on the decontamination properties of the ECA water or the activation of the water in general.

A surface energy reducing agent is added to the electrochemically activated water in order to reduce the surface energy of electrochemically activated water thereby increasing the ability of the electrochemically activated water to penetrate into crevices of items being treated. This is particularly important when cleaning and decontaminating complex medical instruments which may contain microbial contaminants in crevices, joints, and lumens.

Surface energy reducing agents usable in accordance with the present invention include various wetting agents. Such wetting agents include anionic, cationic, nonionic, amphoteric, and/or zwitterionic surfactants. Specific classes of wetting agents which useful include anionic and nonionic surfactants or combinations thereof. Examples of nonionic wetting agents usable in the present invention include surfactants such as fatty alcohol polyglycol ethers, nonylphenoxypoly (ethyleneoxy) ethanol, and ethoxylated polyoxypropylene. Specific examples include Genapol UD-50™ (Oxoalcohol polyglycol ether), Igepal™ (Nonylphenoxypoly (ethyleneoxy) ethanol), Fluowet™ (Fluoroxo-alcohol polyglycol ether), and Pegal™ (Ethoxylated polyoxypropylene). The wetting agents set forth above may be used alone or in combination with each other.

In a first embodiment, corrosion inhibitors such as monosodium phosphate, disodium phosphate, and sodium hexametaphosphate, either alone or in combination, are added to water along with a wetting agent prior to or during electrochemical activation. Addition of such corrosion inhibitors prior to or during electrochemical activation of water, wherein said corrosion inhibitors are passed through the electrolysis unit during actual electrochemical activation of the water, does not decompose the corrosion inhibitory activity of the agent. Further, addition of such corrosion inhibitory agents prior to or during electrochemical activation of the water does not negatively affect the decontamination properties of the activated water. The above treated water is especially useful as a decontamination and/or cleaning agent for stainless steel medical instruments wherein the treated instrument remains free of corrosion but is microbially decontaminated. In addition, the above treated water is highly effective as a rinsing agent for use in conventional sterilization systems. The ECA water acts not only as a rinse but as an antimicrobial-anticorrosive protective rinse. By adding the corrosion inhibitors and wetting agents prior to or during electrochemical activation, the sterilization system and instruments are protected from corrosion and decontamination from the rinse solution.

A second embodiment introduces the corrosion inhibitors and/or wetting agents to the catholyte or anolyte produced after electrolysis of the water. The same advantages described above remain readily realized.

Amounts of corrosion inhibitor and wetting agents to be added to the electrochemically activated water will vary depending upon the type of agent being added and whether or not one or more agents are added.

The inorganic corrosion inhibitors are preferably present in amounts ranging from about 0.01% to 20.0% weight per volume (w/v). Organic corrosion inhibitors are preferably present in amounts ranging from about 0.01% to 5.0% w/v. Phosphates are preferably effective at rates in the range of about 0.01% to about 11.0% w/v.

The wetting agents are preferably present in amounts ranging from about 0.0001% to about 5.0% w/v. More preferably, the wetting agent is present in amounts ranging from about 0.0001% to about 0.5% w/v.

FORMULATION EXAMPLE

An example of a formulation according to the invention is set forth below:

FORMULATION 1

Component 1) Disodium phosphate (DSP) 4.766 g/L (corrosion inhibitor)
Component 2) Monosodium phosphate (MSP) 0.40 g/L (corrosion inhibitor)
Component 3) Sodium hexametaphosphate (HMP) 0.330 g/L (corrosion inhibitor)
Component 4) Genapol 462 µl/L (wetting agent)

The following are examples that illustrate the corrosion inhibiting effectiveness, anti-microbial, and surface tension reducing properties of the compositions of the present invention.

The examples below all utilize the composition identified hereinbefore as Formulation 1. Additionally, the ECA solution was prepared according to the method described hereinbefore.

Surface Tension Reduction

Surface tension of ECA solutions without additives vs. surface tension of ECA solutions with additives (Formulation 1) are given in Table 1:

TABLE 1

| | ECA Solutions Without Additives | ECA Solutions With Additives |
|---|---|---|
| Surface Tension (dynes/cm) | 69.9, 64.1, 72.8 | 28.7, 28.6, 28.0, 28.3, 28.4 |

Note: The surface tension of deionized water at 25° C. is 72.8 dynes/cm.

As can be seen, when using the formulation of the invention with ECA water, surface tension decreased to less than half of the amount present in an untreated ECA solution.

Antimicrobial Properties

D-value comparison for ECA solution without additives vs. ECA solution with additives (Formulation 1) are given in Table 2:

TABLE 2

| Test Solution | Temp., ° C. | n | Avg. linear reg. D-value (sec) | Longest endpoint (sec) | Test organism |
|---|---|---|---|---|---|
| ECA | 20 | 7 | 28.4 ± 6.6 | 240 | B. subtilis |
| ECA w/Formulation 1 | 20 | 1 | 33.0 | 210 | B. subtilis | n = number of tests

As is evident from the above comparison, the additives do not adversely affect the antimicrobial properties of the ECA water.

Corrosion Inhibitory Properties

The data in Table 3 compares the corrosion occurring on materials exposed to ECA water (without additives) and a bleach solution. Both the ECA water and bleach solution have ~300 ppm free chlorine. As can be seen from the results, metallic materials show a more significant degree of degradation than polymeric materials.

As can be seen from Table 4, ECA with Formulation #1 additives substantially reduced corrosion in comparison to untreated ECA and a bleach solution on aluminum, brass, and stainless steel. As noted hereinbefore, these are the main metals used in medical equipment.

An additional test was conducted which compared untreated ECA water with ECA water having Formulation #1 added on PENTAX® medical device components.

TABLE 3

MATERIALS COMPATIBILITY IN ELECTROCHEMICALLY ACTIVE SOLUTION AND BLEACH SOLUTION
The following materials were tested in ECA Solution or in a bleach use dilution (~300 ppm).
One hour of solution exposure is equivalent to 1 cycle.

| MATERIAL | ECA SOLUTION | | BLEACH SOLUTION | |
|---|---|---|---|---|
| | Cycles | Observations | Cycles | Observations |
| Aluminum, 6061-T6 | 24 | ~70% surface discoloration | 24 | ~70% surface discoloration |
| Anodized Aluminum 6061-T6 | 720 | no change | 672 | 75–80% anodization degraded |
| Aluminum 1100 (Calgon Vestal) | 24 | ~50% surface discoloration | 24 | ~70% surface discoloration |
| Anodized Aluminum (Calgon Vestal) | 672 | no change | 672 | 75–80% anodization degraded |
| Brass | 24 | ~50% surface discoloration | 24 | ~70% surface discoloration |
| Borosilicate | 720 | no change | 600 | no change |
| CDA 110 (Calgon Vestal; 99.9% copper) | 24 | ~50% surface discoloration | 24 | ~50% surface discoloration |
| CDA 443 (Calgon Vestal; 75% copper, 28% zinc) | 24 | ~50% surface discoloration | 24 | ~50% surface discoloration |
| Ethylene propylene | 720 | no change | 600 | no change |
| Ethylene propylene diamine (EPDM) | 720 | no change | 600 | no change |
| Fluorosilicone (Viton O-ring) | 720 | no change | 600 | no change |
| Latex (medical glove) | 600 | little elasticity | 600 | elasticity in tact; material "bleached" to white color |
| Polycarbonate | 720 | no change | 600 | no change |
| Polyethylene (high density) | 720 | no change | 600 | no change |
| Polytetrafluoroethylene (Gore-tex tubing) | 600 | no change | 600 | no change |
| Polypropylene | 720 | no change | 600 | no change |
| Polyurethane | 48 | white label slightly discolored; tackiness | N/A | N/A |
| Polyvinyl chloride (Tygon tubing) | 720 | no change | 600 | no change |
| Polyvinyl chloride (Tygon tubing - medical grade) | 720 | no change | 600 | no change |
| Polyvinyl chloride (UPVC) | 720 | no change | 600 | no change |
| Silicone (0-ring) | 720 | cracking | 600 | cracking |
| Stainless Steel 17-4P11 | 24 | <5% surface discoloration; pitting (~3 mm diam.) | 24 | <5% surface discoloration; pitting (~3 mm diam.) |
| Stainless Steel 316L | 24 | <10% surface discoloration | 24 | <2% surface discoloration; pitting (~2 mm diam.) |
| Stainless Steel 316 (Calgon Vestal) | 24 | <10% surface discoloration | 24 | <2% surface discoloration; pitting (~2 mm diam.) |

The data in Table 4 demonstrates the ability of the additives of the invention, such as Formulation 1 above, to reduce corrosion attributed to untreated ECA water.

TABLE 4

ECA SOLUTION MATERIALS COMPATIBILITY SUMMARY
The following materials were tested in ECA solution, Formulation #1, and in a bleach use dilution ~300 ppm).
One hour of solution exposure is equivalent to one cycle. All solutions had a 300 ± 30 ppm
free chlorine concentration, which were evaluated spectrophotometrically.

| | *BLEACH USE DILUTION | *ECA SOLUTION | *FORMULA #1 |
|---|---|---|---|
| Aluminum 6061 | @ 24 cycles: ~70% surface discoloration | @ 24 cycles: ~70% surface discoloration | @ 24 cycles: ~5% surface corrosion |
| Aluminum 6061 - anodized | @ 672 cycles: ~75–80% anodization degraded | @ 24 cycles: no change | @ 24 cycles: no change |
| Brass | @ 24 cycles: ~70% surface discoloration | @ 24 cycles: ~50% surface discoloration | @ 24 cycles: ~10% surface discoloration |
| Stainless Steel 316L | @ 24 cycles: <2% surface corrosion; pitting in small area (~3 mm diam.) | @ 24 cycles: ~10% surface discoloration | @ 24 cycles: ~5% surface discoloration |
| Stainless Steel 17-4PH | @ 24 cycles: <5% surface corrosion; pitting in small area (~3 mm diam.) | @ 24 cycles: ~5% surface corrosion; pitting in small area (~3 mm diam.) | @ 24 cycles: ~2% surface discoloration |

*All solutions had a 300 ± 30 ppm free chlorine concentration, which were evaluated spectrophotometrically.

Below, in Table 5, is a comparative analysis of the results.

TABLE 5

MATERIALS COMPATIBILITY OF PENTAX MEDICAL DEVICE COMPONENTS
IN ELECTROCHEMICALLY ACTIVE SOLUTION OR FORMULA #1
The following materials were tested in ECA Solution with additives, Formula #1 in ECA solution.
One hour of solution exposure is equivalent to one cycle.

| | ECA SOLUTION | | ECA FORMULA #1 SOLUTION | |
|---|---|---|---|---|
| MATERIAL | Cycles | Observations | Cycles | Observations |
| Black, plastic cylinder | 120 | no change | 120 | no change |
| Thin, black collar | 120 | no change | 120 | no change |
| Treated metal tube | 8 | black "specks"—qty increases with time; possible inner corrosion | 120 | no change |
| Screw w/wide threads | 1–120 | 40% surface corrosion at 120 cycles | 120 | no change |
| Screw w/narrow threads | 72 | <1% corrosion | 120 | no change |
| Thin metal piece w/1 hole | 120 | no change | 120 | no change |
| Thin, bent metal piece w/4 holes | 120 | no change | 120 | no change |
| Metal nut | 8–120 | corrosion at 15 minutes; increased corrosion over time; possible leeching of metal-metal binding adhesive | 1–120 | corrosion at 24 hrs.; increased corrosion over time; possible leeching of metal-metal binding sdhesive |
| Air/water valve | | | 120 | no change |
| Metal inlet/outlet port | 1–120 | corrosion at 1 hr; increased corrosion over time; all corrosion appears at soldered joints/pieces | 120 | no change |
| Black,metal sleeve w/threads | | | 120 | no change |

As can be seen from Table 5, those components of PENTAX medical equipment which were susceptible to corrosion due to ECA water were either not corroded when Formulation #1 was added or the corrosion was substantially reduced in the presence of the additives.

Further, testing has been conducted which demonstrates that the functionality of corrosion inhibitors is maintained and not destroyed by circulation through an electrolysis unit during electrochemical activation of water.

The following Example demonstrates that the corrosion inhibition activity of corrosion inhibitors which are added to ECA water during electrochemical activation does not destroy the corrosion inhibitory activity of the corrosion inhibitors.

EXAMPLE 1

Hard water containing 400 ppm $CaCO_3$ was circulated through an electrolysis unit at 12 A (current) and a flowrate of 80L/hr to generate 10.0L of ECA solution having the following properties:

| 10.0L ECA Solution | |
|---|---|
| pH = 8.24 | Conductivity = 10.31 mS/cm |
| free chlorine = 264 ppm | Surface tension = 65.3 dynes/cm |
| Temp. = 50° C. | ORP = 770 mV |

To the 10.0L ECA solution, while in the electrolysis unit, the following components were added:

monosodium phosphate (MSP) at 4.00 g
disodium phosphate (DSP) at 47.66 g
sodium hexametaphosphate (HMP) at 3.30 g
Genapol (wetting agent) at 4620 μL The resulting modified ECA solution had the following properties:

| Modified ECA solution | |
|---|---|
| pH = 7.70 | Conductivity = 14.5 mS/cm |
| Free Chlorine = 246 ppm | Surface Tension = 29.4 dynes/cm |
| Temp = 53° C. | ORP = 805 mV |

Bovine serum art 0.1% was then added to the modified ECA solution.

The bovine/modified ECA solution had the following properties:

| Bovine/Modified ECA solution | |
|---|---|
| pH = 7.69 | Conductivity = 14.5 mS/cm |
| free chlorine = 199 ppm | Surface tension = 29.3 dynes/cm |
| Temp = 53° C. | ORP = 803 mV |

Five coupons of various metals were then introduced into the solution in the electrolysis unit and the solution was allowed to continue to recirculate through the unit. The free chlorine of the solution was monitored during recirculation until it reached 300 ppm. After seven (7) minutes, a twelve (12) minute timer was set and the solution parameters were measured after twelve minutes. The solution, after the twelve (12) minute period had the following properties:

| Modified ECA solution after 12 minute circulation period | |
|---|---|
| pH = 7.86 | Conductivity = 14.86 mS/cm |
| free chlorine = 393 ppm | Surface tension = 30.1 dynes/cm |
| Temp. = 50° C. | ORP = 820 mV |

A control hard water bath was also provided which had 400 ppm (CaCO$_3$) at 53.3° C. (±3° C.). The five coupons were also placed in the control water bath.

The following results were observed from the coupons introduced into the electrolysis unit containing the modified ECA solution according to the invention and from the control hard water bath:

| Metal Coupon | Modified ECA Solution | Control (hard water) |
|---|---|---|
| Brass | <5% Corrosion | NC |
| Aluminum (6061) | NC | NC |
| Anodized Aluminum | NC | NC |
| Stainless Steel 316L (S.S. 316L) | NC | NC |
| Stainless Steel (S.S. 17-4 PH) | NC | NC |

As is evident from the above, even after recirculation through the ECA system for at least 12 minutes, the corrosion inhibitor continued to function to reduce the corrosive properties of the ECA water.

In addition to the above, five additional test runs were conducted in accordance with the procedure of Example 1. The results from these tests are provided below:

| Test No. | 2 | 3 | 4 | 5 | 6 |
|---|---|---|---|---|---|
| 10L ECA | | | | | |
| pH | 7.95 | 8.10 | 8.21 | 8.30 | 8.24 |
| free Cl$^-$ (ppm) | 312 | 340 | 323 | 308 | 337 |
| Temp. (° C.) | 52 | 51 | 54 | 54 | 53 |
| Conductivity (mS/cm) | 11.06 | 11.64 | 11.74 | 10.66 | 11.70 |
| Surface tension (dynes/cm) | 64.0 | 63.8 | 64.1 | 64.0 | 65.4 |
| ORP (mV) | 798 | 804 | 800 | 758 | 796 |
| Modified ECA | | | | | |
| pH | 7.68 | 7.72 | 7.71 | 7.71 | 7.69 |
| free Cl$^-$ (ppm) | 298 | 319 | 298 | 284 | 294 |
| Temp. (° C.) | 53 | 53 | 53 | 54 | 54 |
| Conductivity (mS/cm) | 15.78 | 16.23 | 15.12 | 14.60 | 14.96 |
| Surface tension (dynes/cm) | 28.0 | 27.8 | 31.0 | 27.4 | 28.4 |
| ORP (mV) | 820 | 825 | 820 | 825 | 825 |
| 0.1% Bovine Solution | | | | | |
| pH | 7.70 | 7.73 | 7.69 | 7.65 | 7.71 |
| free Cl$^-$ (ppm) | 250 | 258 | 233 | 228 | 219 |
| Temp. (° C.) | 53 | 53 | 53 | 53 | 53 |
| Conductivity (mS/cm) | 15.71 | 17.5 | 15.28 | 13.81 | 15.7 |
| Surface Tension (dynes/cm) | 28.4 | 28.4 | 29.9 | 28.3 | 28.7 |
| ORP (mV) | 815 | 845 | 840 | 840 | 840 |
| Circulation Time to get 300 ppm Free chlorine (min.) | 4 | 4 | 3 | 4 | 3.5 |
| After 12 minute recirculation | | | | | |
| pH | 7.75 | 7.70 | 7.65 | 7.69 | 7.80 |
| free Cl$^-$ (ppm) | 383 | 408 | 504 | 399 | 453 |
| Temp. (° C.) | 50 | 50 | 51 | 50 | 51 |
| Conductivity (mS/cm) | 15.62 | 17.60 | <20 | 15.28 | 15.3 |
| Surface Tension (dynes/cm) | 32.4 | 30.4 | 31.9 | 30.0 | 30.1 |
| ORP (mV) | 831 | 840 | 850 | 850 | 844 |
| Changes in coupons | | | | | |
| (Test/control) | 2 | 3 | 4 | 5 | 6 |
| Brass | <5%/NC | <5%/NC | <5%/5% (color) | <5%/5% (color) | <5%/>5% (corrosion) |
| Aluminum | NC/NC | NC/NC | NC/NC | NC/NC | NC/NC |
| Anod. Aluminum | NC/NC | NC/NC | NC/NC | NC/NC | NC/NC |
| S.S 316L | <5% (color)/NC | <5% (color)/NC | >5% (color)/NC | >5% (color)/NC | <5% (color)/NC |
| S.S. 17-4 pH | NC/NC | NC/NC | NC/NC | NC/NC | NC/NC |

Based on the results as shown above, it is evident that the functionality of the corrosion inhibitor in the ECA water, during electrochemical activation of the water, did not get destroyed by the electrochemical activation system. Also, the surfactants were not modified during the recirculation because surface tensions did not change significantly.

Further, based on the above comparative tests, the advantages of reduced corrosion and enhanced penetration attained from using ECA water with the above-described corrosion inhibitors and/or surface tension reducing agents are readily apparent wherein the treated ECA water can be utilized without any loss in its biocidal properties.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An anticorrosive decontamination composition comprising:
   a) electrochemically activated (ECA) water as a decontamination agent containing an anolyte possessing anti-microbial properties and a catholyte possessing cleaning properties wherein the anolyte is present in an anti-microbial effective amount and the catholyte is present in an amount effective for cleaning; and,
   b) at least one corrosion inhibitor, which is not decomposed upon passage through an electrolysis unit, in an amount which inhibits corrosion of at least one metal susceptible to corrosion by ECA water wherein the corrosion inhibitor is a copper, brass, aluminum, carbon steel, or stainless steel corrosion inhibitor.

2. The composition of claim 1 wherein the corrosion inhibitor is selected from the group consisting of phosphates, sulfates, molybdates, chromates, dichromates, tungstates, vanadates, borates, benzotriazoles, tolyltriazoles, azoles, benzoates, 8-hydroxyquinoline, ortho-phenylphenol, and combinations thereof.

3. The composition of claim 1 wherein the corrosion inhibitor is a phosphate stainless steel corrosion inhibitor.

4. The composition of claim 3 wherein the phosphate stainless steel corrosion inhibitor is selected from the group consisting of monosodium phosphate, disodium phosphate, sodium tripolyphosphate, sodium hexametaphosphate, benzotriazole, tolyltriazole, sebacic acid, and azoleic acid, or a combination thereof.

5. The composition of claim 1 which further comprises at least one wetting agent in an amount which reduces the surface tension of the electrochemically activated water.

6. The composition of claim 5 wherein the wetting agent is selected from the group consisting of nonionic and anionic wetting agents or combinations thereof.

7. A method for decontaminating medical equipment by contacting said medical equipment with a disinfection effective amount of a composition of claim 1 wherein the medical equipment is contacted for a period of time sufficient to disinfect the medical equipment without corroding the medical equipment.

8. A penetration enhanced decontamination composition comprising:
   a) electrochemically activated (ECA) water as a decontamination agent containing an anolyte possessing anti-microbial properties and a catholyte possessing cleaning properties wherein the anolyte is present in an anti-microbial effective amount and the catholyte is present in an amount effective for cleaning; and,
   b) at least one wetting agent, which is not decomposed upon passage through an electrolysis unit, in an amount which reduces the surface tension of the ECA water, thereby enhancing the penetrability of the ECA water into creviced areas of an object in contact with said ECA water wherein the wetting agent is selected from nonionic and anionic wetting agents or combinations thereof.

9. The composition of claim 8 wherein the wetting agent is selected from fatty alcohol, polyglycol ethers, nonylphenoxypoly (ethyleneoxy) ethanol, and ethoxylated polyoxypropylene or combinations thereof.

10. The composition of claim 8 which further includes a corrosion inhibitor.

11. An anticorrosive decontamination composition comprising:
   a) a liquid microbial decontaminate including electrochemically activated (ECA) water containing an anolyte possessing anti-microbial properties and a catholyte possessing cleaning properties; and,
   b) at least one copper, brass, aluminum, carbon steel, or stainless steel corrosion inhibiting agent which is present in an amount which inhibits corrosion caused by ECA water and which is not decomposed upon passage through an electrolysis unit;
   c) at least one wetting agent selected from a nonionic or anionic wetting agent said wetting agent being present in an amount which reduces the surface tension of the ECA water and which is not decomposed upon passage through an electrolysis unit;
   whereby the composition provides for the penetration of the ECA water into items coming in contact with said ECA water and further wherein the ECA water does not corrode any copper, brass, aluminum, carbon steel or stainless steel surfaces with which it comes in contact.

12. The anticorrosive decontamination composition of claim 11 wherein the corrosion inhibiting agent is present in the range of about 0.01% to about 20.0% w/v and the wetting agent is present in the range of about 0.0001% to about 5.0% w/v.

13. An anticorrosive decontamination composition of claim 11 wherein the corrosion inhibiting agent is selected from the group consisting of monosodium phosphate, disodium phosphate, sodium tripolyphosphate, sodium hexametaphosphate, benzotriazole, tolyltriazole, sebacic acid, and azoleic acid, or a combination thereof.

14. A method for inhibiting corrosion in an electrochemically activated (ECA) water system or sterilization system which contains materials susceptible to corrosion due to ECA water which method comprises:
   adding a corrosion inhibitor which is not decomposed upon passage through the ECA water system, to water in the system;
   electrochemically activating the water without decomposing the corrosion inhibitor to generate corrosion retardant ECA water containing corrosion inhibitor in a sufficient amount to inhibit corrosion caused by ECA water wherein the corrosion inhibitor is added to the ECA system prior to or after electrochemical-activation of the water.

15. The method of claim 14 wherein the corrosion inhibitor includes at least one of a copper, brass, aluminum, carbon steel, and stainless steel corrosion inhibitor.

16. The method of claim 15 wherein the corrosion inhibitor is selected from the group consisting of phosphates, sulfates, molybdates, chromates, dichromates, tungstates, vanadates, borates, benzotriazoles, tolyltriazoles, azoles, benzoates, 8-hydroxyquinoline, ortho-phenylphenol, and combinations thereof.

17. The method of claim 14 wherein the corrosion inhibitor is a phosphate stainless steel corrosion inhibitor.

18. The method of claim 17 wherein the phosphate stainless steel corrosion inhibitor is selected from the group consisting of monosodium phosphate, disodium phosphate, sodium tripolyphosphate, sodium hexametaphosphate, benzotriazole, tolyltriazole, sebacic acid and azoleic acid, and combinations thereof.

19. The method of claim 16 which further includes adding a wetting agent to the ECA system, said wetting agent being present in an amount which reduces the surface tension of the ECA water to provide for the penetration of the ECA water into items coming into contact with said ECA water.

20. The method of claim 19 wherein the wetting agent is selected from the group consisting of nonionic and anionic wetting agents and combinations thereof.

21. The method of claim 19, further wherein a sequestering agent is added to the system.

22. The method of claim 14 further wherein a sequestering agent is added to the system.

23. A method for enhancing the penetration of electrochemically activated (ECA) water containing an anolyte possessing anti-microbial properties and a catholyte possessing cleaning properties wherein the anolyte is present in an anti-microbial effective amount and the catholyte is present in an amount effective for cleaning, said method comprising the step of adding a penetration enhancing effective amount of a wetting agent, which is not decomposed upon passage through an electrolysis unit, to the ECA water wherein the wetting agent is selected from nonionic and anionic wetting agents or combinations thereof thereby enhancing the penetrability of the ECA water into creviced areas of an object in contact with said ECA water.

24. The method of claim 23 wherein the wetting agent is selected from fatty alcohol polyglycol ethers, nonylphenoxypoly(ethyleneoxy) ethanol and ethoxylated polyoxypropylene or combinations thereof.

25. The method of claim 23 which further comprises adding a corrosion inhibitor to the ECA water.

26. A decontamination composition comprising:
  a) electrochemically activated (ECA) water as a decontamination agent;
  b) a copper, brass, aluminum, carbon steel or stainless steel corrosion inhibitor, a wetting agent or a mixture thereof; and
  c) a sequestering agent;
     wherein the decontamination activity of the ECA water is maintained in the presence of components (b) and (c).

27. The decontamination composition of claim 26 wherein the sequestering agent is selected from sodium hexametaphosphate, trisodium nitrolotriacetic acid, and sodium polyacrylates.

28. A decontamination method comprising subjecting an object in need of decontamination to the composition of claim 26, wherein the object is decontaminated without having mineral deposits formed thereon.

* * * * *